(12) United States Patent
Chandler et al.

(10) Patent No.: US 12,357,164 B2
(45) Date of Patent: Jul. 15, 2025

(54) MEDICAL DEVICE INSPECTION SCOPE

(71) Applicant: CLARUS MEDICAL, LLC, Minneapolis, MN (US)

(72) Inventors: Thomas Donald Chandler, Coon Rapids, MN (US); Steven Edward Lombardi, New Brighton, MN (US); Mark Francis Brown, Minnetonka, MN (US); Justin Andrew Hawley, Minneapolis, MN (US); Jerome Steven Stepanek, Eden Prarie, MN (US)

(73) Assignee: Clarus Medical, LLC, Minneapolis, MN (US)

( * ) Notice: Subject to any disclaimer, the term of this patent is extended or adjusted under 35 U.S.C. 154(b) by 0 days.

(21) Appl. No.: 17/591,793

(22) Filed: Feb. 3, 2022

(65) Prior Publication Data

US 2022/0240767 A1 Aug. 4, 2022

Related U.S. Application Data

(63) Continuation-in-part of application No. 17/471,578, filed on Sep. 10, 2021, and a continuation-in-part of
(Continued)

(51) Int. Cl.
*A61B 1/05* (2006.01)
*A61B 1/00* (2006.01)
(Continued)

(52) U.S. Cl.
CPC ............ *A61B 1/05* (2013.01); *A61B 1/00043* (2013.01); *A61B 1/00114* (2013.01);
(Continued)

(58) Field of Classification Search
CPC ............ A61B 1/00043; A61B 1/00114; A61B 1/00117; A61B 1/00124; A61B 1/00126;
(Continued)

(56) References Cited

U.S. PATENT DOCUMENTS 4,860,094 A * 8/1989 Hibino ............... A61B 1/00059
    348/E5.029
4,870,488 A * 9/1989 Ikuno ..................... H04N 13/10
    348/45
(Continued)

FOREIGN PATENT DOCUMENTS

JP    H08-024211 A    1/1996
JP    2005270142 A    10/2005
(Continued)

OTHER PUBLICATIONS

"Bioprinter with Blue-Light Disinfection Minimizes Need for Cleanrooms," Medical Device and Diagnotic Industry [Online]. Retreived from the Internet: URL: www.mddionline.com/3dprinting/bioprinter-blue-light-disinfection- minimizes-need-cleanrooms, published Dec. 31, 2021, 2 pages.

*Primary Examiner* — John P Leubecker

(74) *Attorney, Agent, or Firm* — Merchant & Gould P.C.

(57) ABSTRACT

A medical device inspection system includes a console and a flexible imaging scope. The console includes a housing, a video processor, a light source, a visual display on the housing, and an outlet with two ports. The flexible imaging scope is removably connected to the console via the outlet and includes a CMOS image sensor, an optical fiber bundle, and a connector assembly mounted to a proximal end of the imaging scope. The connector assembly includes an electrical image connector and a light source connector, which plug into the two ports of the outlet to connect the flexible imaging scope to the console.

9 Claims, 4 Drawing Sheets

Related U.S. Application Data application No. 16/351,106, filed on Mar. 12, 2019, now Pat. No. 12,109,081, and a continuation-in-part of application No. 16/253,439, filed on Jan. 22, 2019, now Pat. No. 11,559,597.

(60) Provisional application No. 63/145,066, filed on Feb. 3, 2021, provisional application No. 63/077,025, filed on Sep. 11, 2020, provisional application No. 62/643,856, filed on Mar. 16, 2018, provisional application No. 62/620,847, filed on Jan. 23, 2018.

(51) Int. Cl.
*A61B 1/005* (2006.01)
*A61B 1/06* (2006.01)

(52) U.S. Cl.
CPC .......... *A61B 1/00167* (2013.01); *A61B 1/005* (2013.01); *A61B 1/06* (2013.01); *A61B 1/00059* (2013.01); *A61B 1/00124* (2013.01); *A61B 2562/0223* (2013.01)

(58) Field of Classification Search
CPC . A61B 1/00167; A61B 1/005; A61B 1/00087; A61B 1/00059
USPC ........................................................ 600/132
See application file for complete search history.

(56) References Cited

U.S. PATENT DOCUMENTS

| | | | |
|---|---|---|---|
| 4,905,082 A * | 2/1990 | Nishigaki | A61B 1/07 600/109 |
| 4,918,521 A * | 4/1990 | Yabe | H04N 23/54 600/109 |
| 4,951,135 A * | 8/1990 | Sasagawa | A61B 1/05 348/69 |
| 5,335,662 A * | 8/1994 | Kimura | G02B 23/2484 600/459 |
| 5,626,595 A | 5/1997 | Sklar et al. | |
| 5,833,683 A | 11/1998 | Fuller et al. | |
| 6,095,970 A * | 8/2000 | Hidaka | A61B 1/00124 600/172 |
| 6,520,908 B1 * | 2/2003 | Ikeda | A61B 1/00066 600/110 |
| 8,593,626 B2 | 11/2013 | Brouwer | |
| 8,933,416 B2 | 1/2015 | Arcand et al. | |
| 9,354,182 B2 | 5/2016 | Rochette et al. | |
| 10,245,339 B2 | 4/2019 | Shin et al. | |
| 10,279,058 B2 | 5/2019 | Lin et al. | |
| 10,543,058 B2 | 1/2020 | Bauco et al. | |
| 10,705,020 B2 | 7/2020 | Baribeau | |
| 10,709,313 B2 | 7/2020 | Stephenson | |
| 2004/0064019 A1 * | 4/2004 | Chang | A61B 1/045 600/118 |
| 2005/0157168 A1 * | 7/2005 | Kaneko | A61B 1/000095 348/72 |
| 2007/0162095 A1 * | 7/2007 | Kimmel | A61B 1/042 600/172 |
| 2008/0159908 A1 | 7/2008 | Redmond | |
| 2008/0195128 A1 * | 8/2008 | Orbay | A61B 1/00048 600/183 |
| 2009/0099420 A1 | 4/2009 | Woodley et al. | |
| 2009/0290374 A1 * | 11/2009 | Tashiro | A61B 1/0669 362/574 |
| 2010/0217080 A1 | 8/2010 | Cheung et al. | |
| 2011/0116675 A1 * | 5/2011 | Terlizzi | H04R 1/1083 381/384 |
| 2012/0059255 A1 | 3/2012 | Paul et al. | |
| 2012/0071895 A1 | 3/2012 | Stahler et al. | |
| 2013/0008233 A1 * | 1/2013 | Kosugi | A61B 1/00128 73/40.5 R |
| 2013/0035550 A1 * | 2/2013 | Watanabe | G02B 23/2484 600/132 |
| 2014/0094656 A1 * | 4/2014 | Matsukawa | A61B 1/00114 600/110 |
| 2015/0012021 A1 | 1/2015 | Mihara | |
| 2015/0182106 A1 | 7/2015 | King | |
| 2015/0231287 A1 | 8/2015 | Lin et al. | |
| 2015/0272426 A1 * | 10/2015 | Narita | A61B 1/00124 600/132 |
| 2016/0088999 A1 * | 3/2016 | Langell | H04N 23/663 348/68 |
| 2016/0089001 A1 * | 3/2016 | Hara | A61B 1/00029 600/109 |
| 2016/0353973 A1 | 12/2016 | Mirza et al. | |
| 2017/0035277 A1 | 2/2017 | Kucharski et al. | |
| 2019/0038789 A1 | 2/2019 | Kang et al. | |
| 2019/0038791 A1 | 2/2019 | Gerrans et al. | |
| 2019/0224357 A1 | 7/2019 | Sundet et al. | |
| 2019/0246884 A1 * | 8/2019 | Lu | A61B 1/018 |
| 2019/0247050 A1 | 8/2019 | Goldsmith | |
| 2019/0282327 A1 | 9/2019 | Sundet et al. | |
| 2019/0290104 A1 | 9/2019 | Culman et al. | |
| 2019/0357751 A1 | 11/2019 | Friedlander et al. | |
| 2019/0357753 A1 * | 11/2019 | Shigehisa | A61B 1/00186 |
| 2021/0213148 A1 | 7/2021 | Gerrans et al. | |
| 2021/0339297 A1 | 11/2021 | Stephenson | |
| 2021/0386443 A1 | 12/2021 | Heimberger | |
| 2022/0080469 A1 | 3/2022 | Sundet et al. | |
| 2023/0233724 A1 | 7/2023 | Sundet et al. | |

FOREIGN PATENT DOCUMENTS

| | | |
|---|---|---|
| WO | 2017034908 A1 | 3/2017 |
| WO | 2020023778 A1 | 1/2020 |
| WO | 2020096888 A1 | 5/2020 |
| WO | 2020096889 A1 | 5/2020 |
| WO | 2020096890 A1 | 5/2020 |
| WO | 2020096891 A1 | 5/2020 |
| WO | 2020096892 A1 | 5/2020 |
| WO | 2020096893 A1 | 5/2020 |
| WO | 2020096894 A1 | 5/2020 |
| WO | 2020123679 A1 | 6/2020 |

\* cited by examiner

MEDICAL DEVICE INSPECTION SCOPE

CROSS-REFERENCE TO RELATED APPLICATIONS

The present application claims priority to U.S. provisional application 63/145,066 filed Feb. 3, 2021 and is a continuation-in-part of each of: (a) U.S. non-provisional application patent application Ser. No. 17/471,578 filed Sep. 10, 2021, which claims priority to U.S. provisional patent application 63/077,025 filed Sep. 11, 2020; (b) U.S. non provisional patent application Ser. No. 16/351,106 filed Mar. 12, 2019, which claims priority to U.S. provisional patent application 62/643,856 filed Mar. 16, 2018; and (c) U.S. non-provisional application Ser. No. 16/253,439, filed Jan. 22, 2019, which claims priority to U.S. provisional patent application 62/620,847 filed Jan. 23, 2018. The present application claims priority to each of the noted applications and hereby incorporates by reference the content of each application in its entirety.

TECHNICAL FIELD

This application is directed to medical devices, systems and methods. More specifically, the application is directed to a scope for facilitating the inspection of medical devices.

BACKGROUND

Millions of medical devices are used in hospitals throughout the world every day. With the continuing advancement of medical and surgical procedures over time, one of the trends is toward minimally invasive procedures performed through smaller incisions or even through the body's natural orifices. Examples of this trend include arthroscopic surgery, transcatheter aortic valve replacement ("TAVR"), natural orifice transluminal endoscopic surgery ("NOTES"), robotic surgery and many others. Many of these procedures involve the use of long, flexible catheter instruments and/or long, flexible endoscopes for visualizing the procedure. Additionally, endoscopes are used in countless different diagnostic and therapeutic procedures in many parts of the body.

One of the challenges with the use of endoscopes, fiber scopes, catheter-based medical/surgical instruments and other long, thin, reusable instruments is how to properly and effectively clean them. Many endoscopes and other instruments are too expensive to be disposable and so must be reused. Long, small-diameter, flexible instruments can be extremely hard to clean on the inside. They are also hard to inspect on the inside. Not only can flexible instruments collect bacteria and other contaminants, but they can also crack or become otherwise permanently deformed during use, for example when the instrument is bent or kinked. These instruments are typically processed in a cleaning facility located within the hospital, by workers with very little training. One way to inspect the inside of such instruments is to advance a small, flexible scope through the lumen(s) of the device, so that contaminants and damage can be seen. It can be difficult, however, for the person doing the inspection to effectively identify contaminants and internal damage to the device. Thus, the inspection process can be labor intensive and sometimes ineffective. It can also be hard to find a scope small enough to fit through the lumens of some medical devices while allowing for adequate visualization. Additionally, once contamination of an endoscope or catheter lumen (or similar inner portion of a medical device) is identified, it can often be difficult to adequately clean the lumen.

Therefore, it would be desirable to have improved devices, systems and methods for inspecting and possibly even disinfecting medical devices, specifically endoscopes, catheters and other long, thin, flexible medical devices that are difficult to inspect on the inside. At least some of these objectives are addressed in this application.

SUMMARY

In one aspect of the present disclosure, a medical device inspection system includes a console and a flexible imaging scope. The console includes a housing, a video processor, a light source, a visual display on the housing, and an outlet with two ports. The flexible imaging scope is removably connected to the console via the outlet and includes a CMOS image sensor, an optical fiber bundle, and a connector assembly mounted to a proximal end of the imaging scope. The connector assembly includes an electrical image connector and a light source connector, which plug into the two ports of the outlet to connect the flexible imaging scope to the console.

In various embodiments, the console is compatible with at least one additional flexible imaging scope that has at least one different characteristic from the flexible imaging scope. For example, the different characteristic may be image size, scope diameter and/or scope length. In some embodiments, the video processor is configured to process images from multiple different CMOS sensors with different pixel sizes in different flexible imaging scopes.

The connector assembly of the flexible imaging scope may include a permanent magnet, and the console may include a magnetic sensor inside the outlet, to detect the permanent magnet when the connector assembly is plugged into the outlet. The permanent magnet may be configured to indicate to the console a pixel size of the CMOS image sensor. The magnetic sensor may detect the pixel size from the permanent magnet and provide the pixel size to the video processor of the console.

In another aspect of the present disclosure, a method for inspecting a medical device involves plugging a first connector assembly of a first flexible imaging scope into an outlet of a console, where the first connector assembly comprises an electrical image connector and a light source connector. The method then involves identifying a first pixel size of a first image sensor of the first flexible imaging scope with a processor of the console and inspecting the medical device with the first flexible imaging scope. Optionally, the method may further involve unplugging the first flexible imaging scope from the console, plugging a second connector assembly of a second flexible imaging scope into the outlet of the console, identifying a second pixel size of a second image sensor of the second flexible imaging scope with the processor of the console, wherein the first pixel size and the second pixel size are different, and inspecting the medical device with the second flexible imaging scope.

The method may also involve selecting the first flexible imaging scope from a group of multiple different imaging scopes, where at least some of the multiple different imaging scopes have different pixel sizes, and the processor of the console is configured to process images from the multiple different imaging scopes. Identifying the first pixel size may involve sensing a permanent magnet in the connector assembly of the first flexible imaging sensor with a magnetic sensor of the console and providing sensed data from the magnetic sensor to the processor of the console.

These and other aspects and embodiments are described more fully below, in reference to the attached drawing figures.

DETAILED DESCRIPTION

Disclosed in this application are various examples of an endoscope (or simply "scope"), which may be used for inspecting the inside of medical devices or for any other suitable purpose. For example, the scope may be inserted into a lumen of a larger endoscope and advanced through the lumen to detect imperfections, damage, contamination and/or the like inside of the endoscope. In this way, the scope described in this application may help a user inspect a medical device that is being cleaned, sterilized or otherwise processed for reuse. In some embodiments, the scope may be designed not only to help visualize imperfections and contamination of a medical device lumen but also to disinfect or otherwise clean the lumen. These concepts and many others are described in greater detail below. The examples of various features and embodiments of the scope described below are not intended to limit the scope of the invention but are provided for descriptive purposes only.

Figure 1:
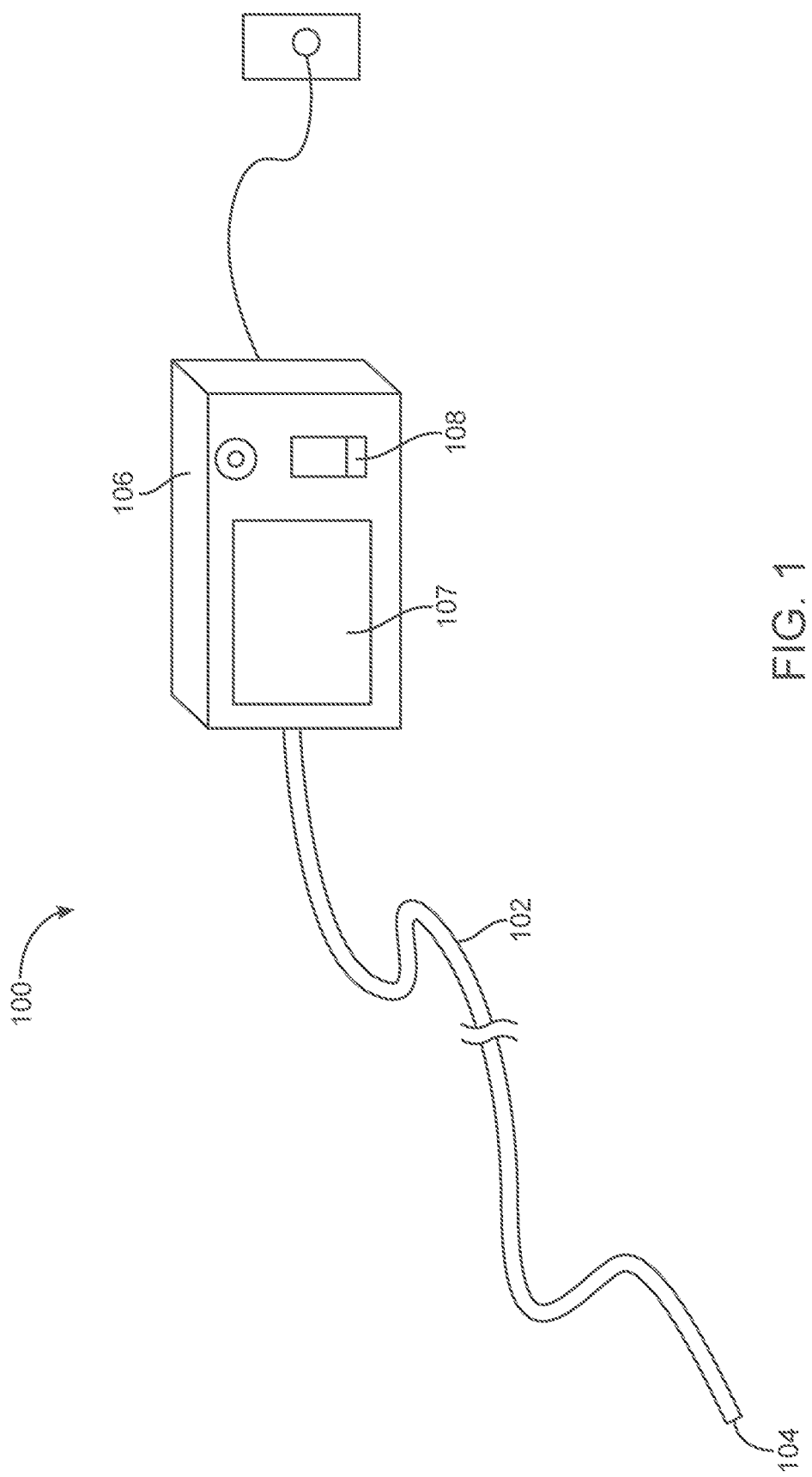
FIG. 1 is a perspective view of a medical device inspection scope, according to one embodiment.

Referring now to FIG. 1, in one example, an elongate, medical device inspection scope 100 includes an outer layer 102 (or "outer housing") and a distal end 104. The proximal end of the scope 100 is attached to a camera body/light source 106, which may sometimes be referred to as a "box." In some embodiments, the outer layer 102 of the scope 100 may have a specific diameter, sized to be able to fit within lumens of various endoscopes, catheters and/or other medical devices for inspection purposes. For example, in various embodiments, the outer layer 102 may have an outer diameter of less than 2 millimeters, and in some embodiments less than 1 millimeter.

In one embodiment, the camera body/light source 106 may include a display 107 and one or more controllers 108. The display 107 may display an image of the inside of the medical device being examined, or it may display data related to the inside of the medical device and/or the scope 100. In some embodiments, the camera body/light source 106 may connect to a separate display monitor for displaying images captured by the scope 100. The controllers 108 may include an on/off power switch and any other switch, knob, controller or the like.

In some embodiments, the scope 100 is configured to (1) emit illuminating light and capture still and/or video images of the inside of a medical device and (2) emit cleaning/disinfecting light, such as UV light, UVC light, and/or visible cleaning/disinfecting light (e.g., light having a wavelength from 400 nm to 500 nm, which is blue light that is safe for humans but kills most, if not all, forms of bacteria, yeast, and mold) to clean/disinfect the inside/lumen of the medical device. Such an embodiment may be configured such that the user can switch back and forth between visible/illumination light and cleaning/disinfecting light emission, and/or the user may in some cases emit both types of light simultaneously. In such embodiments, the controllers 108 may include a function control switch, button, knob or the like, for switching back and forth between illumination mode, cleaning/disinfecting mode and in some examples a combination light mode. In one embodiment, the light selection controller 108 may be a mechanical switch that allows the operator to toggle between visible/illumination light and cleaning/disinfecting light. The switch may be rotary or leveler action and may be hand or foot operated. In another embodiment, the controller 108 may be an electronically activated switch, such as an electronic button on the display 107 or another screen, to switch between visible and cleaning/disinfecting light. Embedded software, for example residing in the light source/box 106, may be configured to control the cleaning/disinfecting light energy dwell time (on/off/pulsed—e.g., the amount of energy delivered over a specific time period) and intensity. In one embodiment, a connector (not shown) splices the two different inputs (i.e., the visible light and the cleaning/disinfecting light) into one single output, while preventing the individual light energies from escaping and while withstanding the caustic nature of UVC light (or other disinfecting/cleaning light). In one embodiment, both wavelengths enter a housing through a standard connection point (not shown) and are then spliced into one exit point. In various examples, any suitable splice connector may be used.

Figure 2:
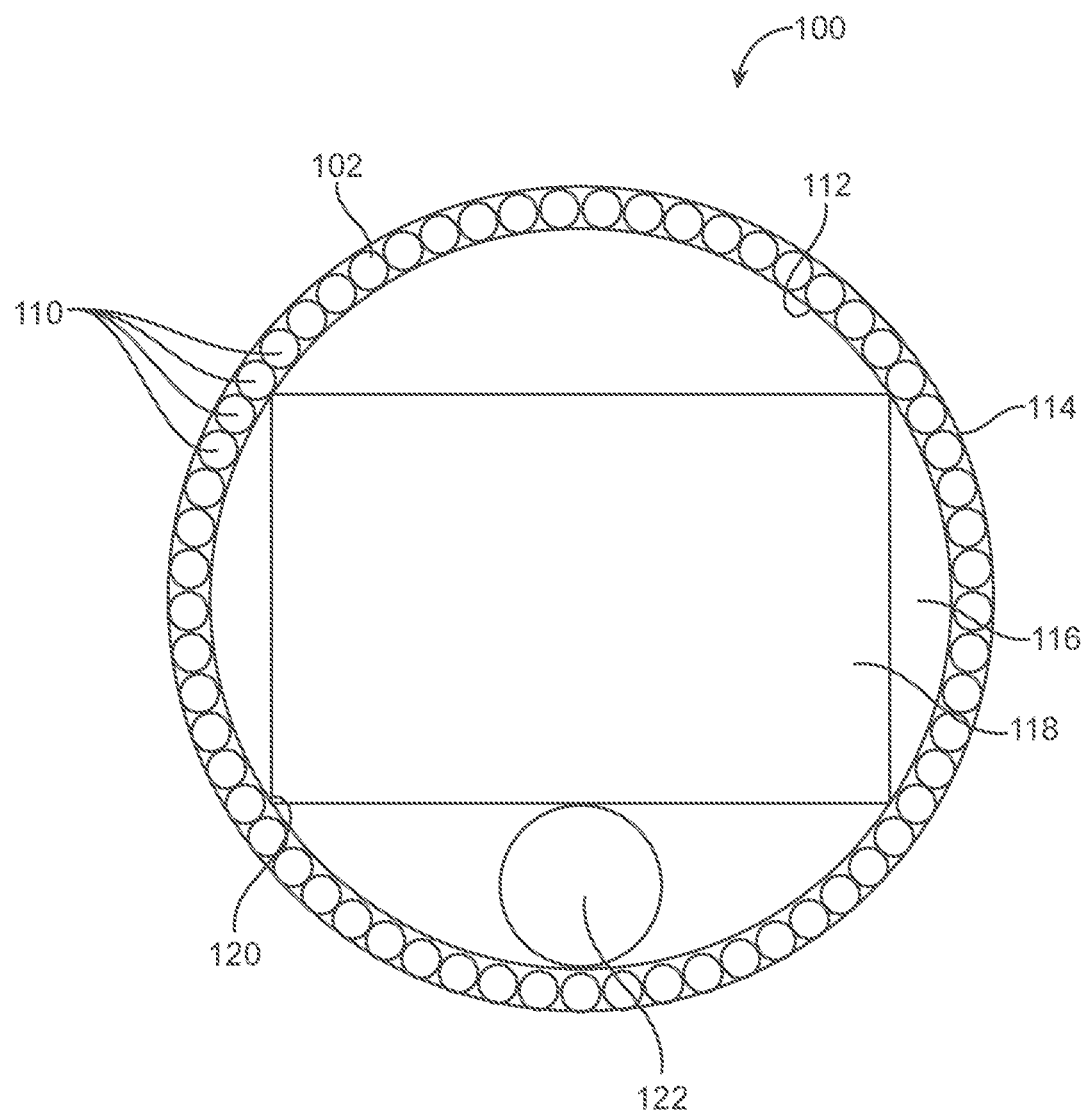
FIG. 2 is a cross-sectional view of the inspection scope of FIG. 1.

Referring to FIG. 2, the scope 100 of FIG. 1 is illustrated in cross section. As seen in this figure, the scope 100 includes the outer layer 102 and an inner layer 112, which together form a circumferential space 114 between the two. Again, in some embodiments, the outer diameter of the outer layer 102 may be less than 2 millimeters, or in some examples less than 1 millimeter. Multiple light fibers 110 (or "illumination fibers"), which transmit light from the light source 106 to the distal end 104 of the scope 100, may be positioned inside the circumferential space 114 (as illustrated), inside the central lumen 116, or both. Inside the inner layer 112 is a central lumen 116, which contains a camera module 118 and an optional elongate stiffening member 122. In this embodiment, the camera module 118 has a rectangular cross-sectional shape. In an alternative embodiment, the corners 120 of the camera module may be shaved, sanded or otherwise smoothed or rounded off.

As mentioned above, in some embodiments, the light fibers 110 are configured to emit visible light for illumination purposes and cleaning/disinfecting light, such as UV light, UVC light, and/or visible spectrum blue light for disinfecting the inside of a medical device. As UVC light can be highly caustic, it is important to transmit the light down the length of the light fibers 110 carefully, to prevent its unintended release. In some embodiments, each of the light fibers 110 may include a silica core, a doped silica clad, a polyimide layer, and a buffer made of polyimide, silicone, acrylate, fluoropolymer or other suitable buffer material. These are merely examples, however, and in alternative embodiments other materials or combinations may be used. In some embodiments, all the light fibers 110 may be configured to transmit visible light and UV light. In alternative embodiments, one set of fibers 110 may be configured to transmit visible light, and another set of fibers 110 may be configured to transmit UV light.

The stiffening member 122 is an optional component, used in some embodiments to enhance/increase the rigidity of the scope 100, to prevent over-bending or kinking. The stiffening member 122 may have any suitable size, length, shape and material, according to various embodiments. In some embodiments, for example, the stiffening member 122 may be a fiber, such as a glass or plastic fiber with a coating. In one embodiment, the stiffening member 122 may be a laser fiber, which in the scope 100 is not used for transmitting light but only as a piece to add rigidity to the scope 100.

In one embodiment, a method for making the medical device inspection scope 100 may involve positioning the inner layer 112 inside the outer layer 102, then placing the multiple light fibers 110 inside the circumferential space 114. The camera module 116 and laser fiber 122 may then be placed in the inner lumen 116 of the scope 100. In one example, the method of making the scope 100 may also include shaving, sanding or otherwise smoothing off corners 120 of the camera module 118.

A method for using the medical device inspection scope 100 may involve inserting the distal end 104 of the scope 100 into a lumen of a medical device, such as an endoscope, catheter or any other suitable device. The scope 100 is then advanced through the lumen, while the light fibers 110 are used to illuminate the lumen, and the camera module 116 is used to capture video and/or still images of the lumen. Some embodiments may include a processor for storing and/or interpreting data acquired by the camera module. For example, in some embodiments, the processor may be configured to identify irregularities or defects in the inside of an endoscope, catheter or other medical device.

Figure 3A:
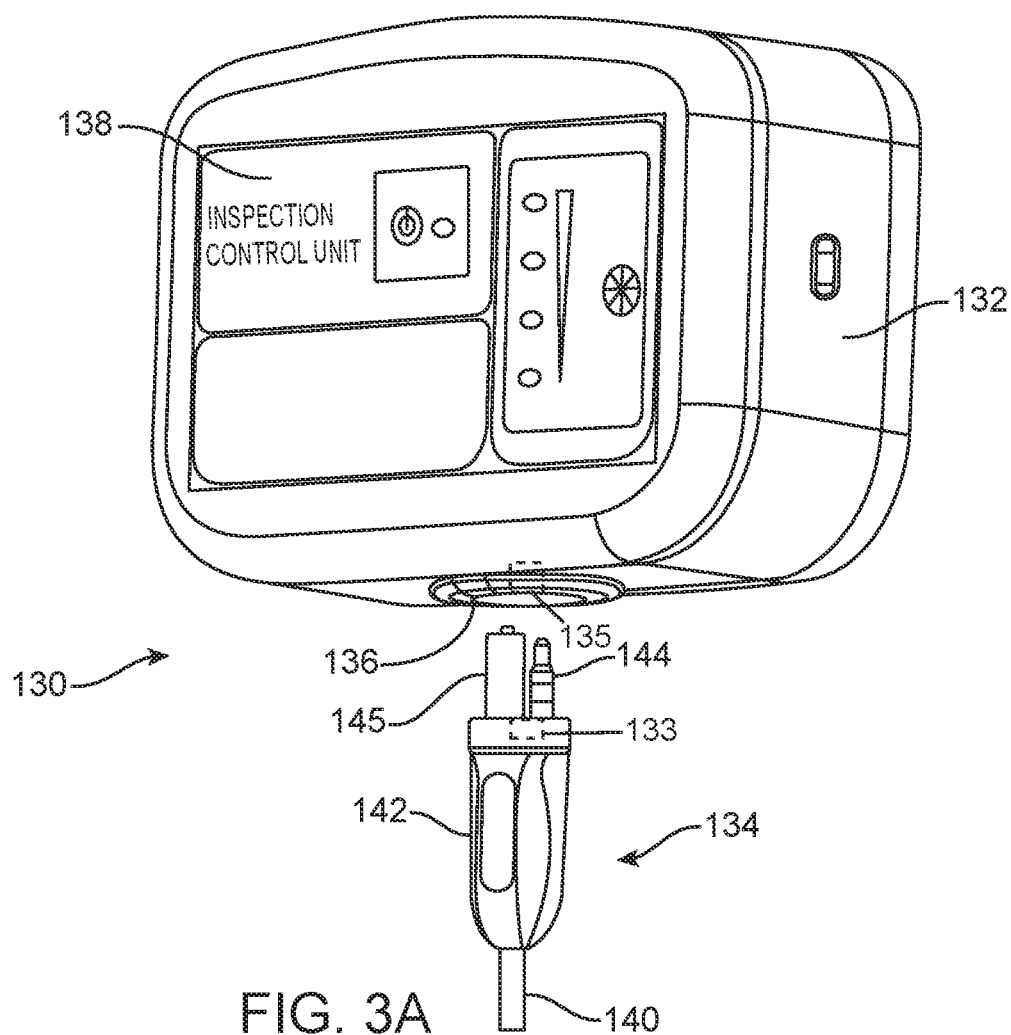
FIG. 3A is a perspective view of a medical device inspection system including a console and a flexible imaging scope according to one embodiment.
Figure 3B:
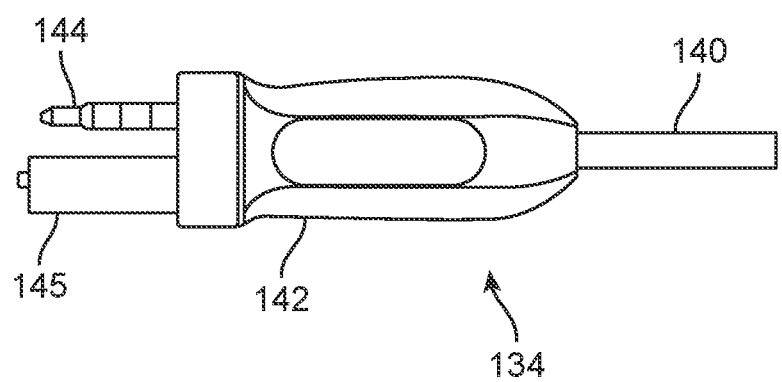
FIG. 3B is a side view of a proximal portion of the flexible imaging scope, according to one embodiment.

Referring now to FIG. 3A, an imaging scope system 130 is illustrated, according to one embodiment. In this embodiment, the system 130 includes a console 132 (or "controller housing") and an imaging scope 134. The console 132 includes a display panel 138 and an outlet 136. The imaging scope 134, only a portion of which is shown, includes an imaging cable 140 (which extends to a distal imaging tip, at an opposite end not shown here) attached to a connector assembly 142, which includes an electrical image connector 144 and a light source connector 145. FIG. 3B shows the proximal end of the imaging scope 134 in a slightly larger view. In this embodiment, the imaging scope 134 is removable from the console 132, via the plug 142 and the outlet 136. The electrical image connector 144 and a light source connector 145 plug into two corresponding ports of the outlet 136 to connect the imaging scope 134 to the console 132. This allows the imaging scope 134 to be swapped out for a different imaging scope. Different imaging scopes 134 may have different lengths, diameters, and pixel sizes. For example, the imaging scope 134 may have a 2 mm dimeter, with an image size of 400×400 pixels, or alternatively a 1 mm diameter with an image size of 200×200 pixels. These are merely two examples. The imaging scope 134 includes both an image sensor and an illumination light fiber bundle, and it is terminated in the connector assembly 142 with the electrical image connector 144 and the light source connector 145. In this embodiment of the imaging scope 134, the electrical image connector 144 and the light source connector 145 are arranged side-by-side on the connector assembly 142. In alternative embodiments, however, other configurations may be used. For example, the electrical image connector 144 and the light source connector 145 may be coaxially arranged, with the image fiber bundle within the center pin of a stereo plug.

The console 132 may include an adjustable light source and a video processor that is electrically switchable to process images from either a 400×400 pixel sensor or a 200×200 sensor, for example. In some embodiments, a permanent magnet 133 may be incorporated into the connector assembly 142 of the image scope 134, and the mating outlet 136 in the console 132 may contain a magnetic switch 135 to sense which imaging scope is plugged in. The video processor may then be automatically configured, based on the magnetic signal input.

Previously described systems do not include an imaging scope that combines light and image signal into one connector. They also do not include a video processor that can handle multiple sizes of image sensors or a magnetic sensor built into a connector to indicate to the processor which image sensor is plugged in.

Figure 4:
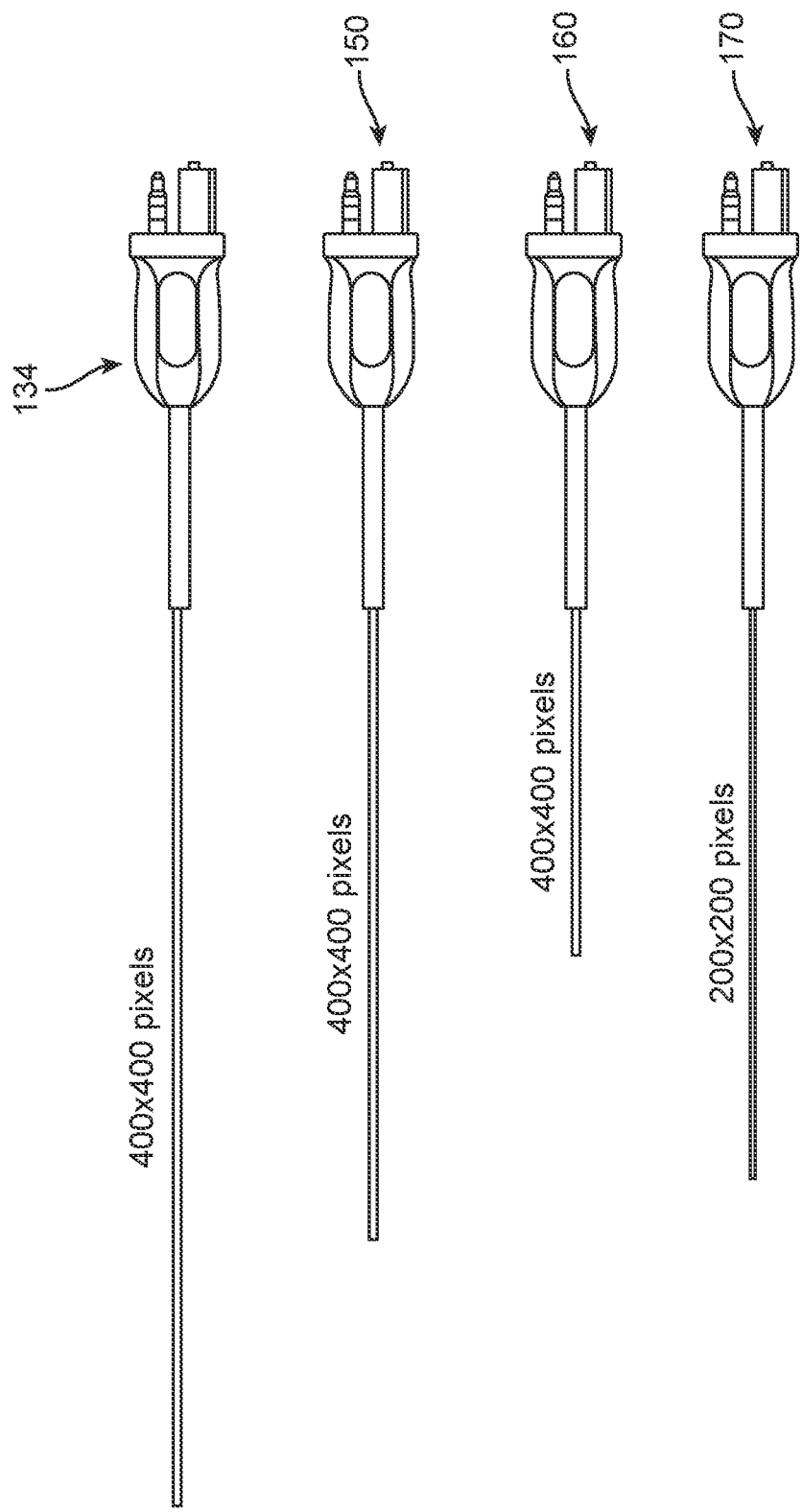
FIG. 4 is a side view of four different embodiments of a flexible imaging scope, which are compatible with the console of FIG. 3A.

FIG. 4 is a side view of the imaging sensor 134 and several alternative embodiments of imaging sensors 150, 160, 170, which may be used interchangeably with the console 132. As indicated in FIG. 4, the imaging sensor 134 has an image size of 400×400 pixels and is 1.8 m long. Another imaging sensor 150 may have an image size of 400×400 pixels and be 1.1 m long. Another imaging sensor 160 may have an image size of 400×400 pixels and be 0.7 m long. And yet another imaging sensor 170 may have an image size of 200×200 pixels and be 1.0 m long. In various embodiments, imaging sensors for use with the console 132 may have any suitable diameter, length and image size, including but not limited to those shown in FIG. 4.

The above description is intended to be a complete description of one embodiment of a small diameter endoscope for inspecting medical devices and potentially other uses. It is meant to be a description of examples only and is not intended to limit the scope of the invention.

We claim:

1. A system comprising:
  a console comprising:
    a housing;
    a video processor in the housing;
    a visual display in communication with the video processor; and
    an outlet on the housing comprising two ports; and
  an imaging scope removably connected to the console via the outlet, the imaging scope comprising:
    an elongate imaging cable having a proximal end and a distal end, the distal end including a distal imaging tip;
    a plug arranged at the proximal end of the imaging cable to connect the imaging scope to the outlet of the console, the plug comprising:
      a single connector body having a face surface, the single connector body forming a handle of the plug; and
      only two prongs extending from the face surface of the single connector body, the two prongs comprising:
        a stereo audio-type prong comprising multiple electrical contacts arranged along a length of the stereo audio-type prong; and
        a fiber-optic prong including at least one optical fiber arranged within the fiber-optic prong.

2. The system of claim 1, wherein the console is compatible with at least one additional imaging scope that has at least one different characteristic from the imaging scope, and wherein the at least one different characteristic is selected from the group consisting of image size, diameter, and length.

3. The system of claim 1, wherein the video processor is configured to process images of different image resolutions from multiple different CMOS sensors in different imaging scopes.

4. The system of claim 1, wherein the single connector body of the plug of the imaging scope further comprises a permanent magnet, and wherein the console further comprises a magnetic sensor inside of the outlet to detect the permanent magnet when the plug is plugged into the outlet.

5. The system of claim 4, further comprising a CMOS image sensor, wherein the permanent magnet is configured to indicate to the console a pixel size of the CMOS image sensor.

6. The system of claim 5, wherein the magnetic sensor detects the pixel size from the permanent magnet and provides the pixel size to the video processor of the console.

7. The system of claim 1, wherein the system is a medical device inspection system.

8. A system comprising a console comprising:
   a housing;
   a video processor in the housing;
   a visual display in communication with the video processor; and
   a single outlet on the housing configured to receive a plug of an imaging scope, the single outlet comprising only two ports comprising:
   a first port being configured to connect with a stereo audio-type prong having multiple electrical contacts arranged along a length of the stereo audio-type prong; and
   a second port being configured to connect with a fiber-optic prong including at least one optical fiber arranged within the fiber-optic prong.

9. An imaging scope comprising:
   an elongate imaging cable having a proximal end and a distal end, the distal end including a distal imaging tip;
   a plug arranged at the proximal end of the imaging cable to connect the flexible imaging scope to a receptacle of a console, the plug comprising:
   a single connector body having a face surface, the single connector body forming a handle of the plug; and
   only two prongs extending from the face surface of the single connector body, the two prongs comprising:
   a stereo audio-type prong comprising multiple electrical contacts arranged along a length of the stereo audio-type prong; and
   a fiber-optic prong including at least one optical fiber centered within the fiber-optic prong.

* * * * *